United States Patent
Kokubu et al.

(10) Patent No.: US 6,680,471 B2
(45) Date of Patent: Jan. 20, 2004

(54) ILLUMINATING APPARATUS AND METHOD FOR ILLUMINATING A CURVED SURFACE

(75) Inventors: Takao Kokubu, Kodaira (JP); Toru Kitajima, Kodaira (JP)

(73) Assignee: Bridgestone Corporation, Tokyo (JP)

(*) Notice: Subject to any disclaimer, the term of this patent is extended or adjusted under 35 U.S.C. 154(b) by 0 days.

(21) Appl. No.: 10/101,721

(22) Filed: Mar. 21, 2002

(65) Prior Publication Data
US 2002/0134910 A1 Sep. 26, 2002

(30) Foreign Application Priority Data
Mar. 23, 2001 (JP) ........................ 2001-085632

(51) Int. Cl.[7] ............. H01J 40/14; G02F 1/01
(52) U.S. Cl. ....................... 250/225; 73/146
(58) Field of Search ............. 250/205, 239, 250/208.2, 214 R, 578.1, 223 R, 559.39–559.4, 559.08, 559.19, 559.21–559.22; 356/394, 240.1, 426–429, 237.2, 121, 213, 218, 221, 222, 445; 73/146–146.8, 800; 702/35

(56) References Cited

U.S. PATENT DOCUMENTS

| | | | |
|---|---|---|---|
| 4,910,411 A | * | 3/1990 | Teraguchi et al. ..... 250/559.44 |
| 4,959,537 A | | 9/1990 | Kimoto et al. |
| 4,972,093 A | * | 11/1990 | Cochran et al. ....... 250/559.08 |
| 5,042,915 A | * | 8/1991 | Akutsu et al. .............. 359/230 |
| 5,963,328 A | * | 10/1999 | Yoshida et al. ............. 356/600 |
| 6,441,896 B1 | * | 8/2002 | Field .......................... 356/222 |

FOREIGN PATENT DOCUMENTS

EP       1 043 578 A2    10/2000

* cited by examiner

Primary Examiner—David Porta
Assistant Examiner—Patrick Lee
(74) Attorney, Agent, or Firm—Oliff & Berridge, PLC (57) ABSTRACT

There is disclosed an apparatus in which when a surface having a curved portion, for example, a tire surface is visually inspected, light is uniformly illuminated on the surface. In this apparatus, an image pickup operation is performed by a CCD for a region to be visually inspected, which is illuminated by turning on LEDs. Based on the image pickup result, a density distribution of the region to be visually inspected is prepared. A difference between a target light quantity and light quantity, which is obtained for each field angle of the density distribution at which the region to be visually inspected is illuminated by each light source unit, is calculated and corrected. This correction allows the quantity of light reflected from the region to be visually inspected on the inner peripheral surface to become uniform.

20 Claims, 7 Drawing Sheets

ILLUMINATING APPARATUS AND METHOD FOR ILLUMINATING A CURVED SURFACE

BACKGROUND OF THE INVENTION

1. Field of the Invention

The present invention relates to illuminating method and apparatus in which, when the outer appearance of a surface having a curved portion is inspected, the surface to be inspected is illuminated.

2. Description of the Related Art

Conventionally, as an apparatus in which, when the outer appearance of a curved surface, particularly, an inner peripheral surface of a concave member is inspected, the curved surface to be inspected is illuminated without causing local reflection unevenness, a diffuser such as a light diffusion filter or a light diffusion plate is provided for a light source. The use of the diffuser allows light to be evenly spread all over a region to be illuminated.

Alternatively, a fluorescent light in which a light source itself emits diffused light may be selected. The fluorescent light includes an inner peripheral surface of a cylinder-shaped fluorescent pipe which is coated with a light diffusion material. Therefore, the fluorescent light itself has the same effect as that of the aforementioned diffuser.

Further, it is also considered that uniformity of light from a light source is realized by providing an arrangement of a plurality of point light sources each having a small quantity of light, for example, light emitting diodes (LED). Although each having a small quantity of light, LED allows diffusion of light over a wide region and can be regarded as a surface light source.

According to the light source having the aforementioned structure, a required sufficient quantity of light can be obtained when the outer appearance of an inner peripheral surface of a concave member is visually inspected. An inner peripheral surface of a tire is an example of the concave member.

However, the inner peripheral surface of the tire applied as the concave member is bent in a three-dimensional manner. From the standpoint of a tire structure, an opening is formed at an inner side of a donut-shaped structure and irregularities are provided on a concave inner peripheral surface. Accordingly, in the light source having the aforementioned structure, light is difficult to reach up to a rear side of a convex portion, and even if light is uniformly emitted from a light source, the quantity of light received by an inner surface which is practically irradiated with light becomes ununiform. The quantity of light received is the quantity of reflected light, alternatively. As a result, outer appearance inspection cannot properly be carried out.

SUMMARY OF THE INVENTION

In view of the aforementioned circumstances, an object of the present invention is to provide an illuminating apparatus in which when the outer appearance of a surface having a curved portion is inspected, light can be evenly illuminated on the surface to be inspected and outer appearance inspection can be properly carried out.

A first aspect of the present invention is an illuminating apparatus in which when an outer appearance of a surface having a curved surface is inspected, the surface to be inspected is illuminated, comprising: a density detecting device which is capable of detecting a density of at least a region whose outer appearance is to be inspected; a light source unit provided with a predetermined number of light emitting portions which emit light for illuminating the region whose outer appearance is to be inspected, and also provided with a base plate having the predetermined number of light emitting portions and made of a flexible material; a locating device for locating the light source unit along a curvature of the surface at a predetermined space to a surface of the region whose outer appearance is to be inspected; and an emitted-light-quantity control device for controlling a quantity of light from the light emitting portions based on a result of detection by the density detecting device.

The illuminating apparatus includes the light source units which are provided by the locating device along the surface of a region whose outer appearance is to be inspected. As a result, the light source units are substantially disposed at a predetermined space to the surface.

However, in a case in which the surface is formed so as to have irregularities, light does not reach up to a concave portion interposed between convex portions. Even if the quantity of light from light emitting portions is made uniform, reflected light from the surface becomes ununiform. As a result, outer appearance inspection is impeded.

Accordingly, in the present invention, the density of the region whose outer appearance is to be inspected is detected by the density detecting device, and based on the result of detection, the quantity of light from the light emitting portions is increased or decreased. In a case in which a plurality of light source units are used, the quantity of light may be increased or decreased for each light source unit.

In other words, the quantity of light from a light source unit corresponding to a region to which light does not reach is increased, and the quantity of light from a light source unit corresponding to a region in which the quantity of reflected light locally increases due to irregular reflection or the like is decreased. As a result, the quantity of light reflected from the region to be visually inspected can be made substantially uniform, and outer appearance inspection for checking whether there is a flaw or the like can be properly carried out.

In the present invention, preferably, the emitted-light-quantity control device is formed by: a density distribution preparing device for, based on a detection result of density from the density detecting device, preparing a density distribution of the region whose outer appearance is to be inspected; and an emitted-light-quantity increase/decrease device for increasing or decreasing a quantity of light emitted from the light emitting portions so that the density distribution prepared by the density distribution preparing device is made uniform.

The present invention provides light-quantity control of the light emitting portions. That is, a density distribution of the region whose outer appearance is to be inspected is prepared based on a result of detection by the density detecting device, and the quantity of light emitted from the light emitting portions is increased or decreased so that the prepared density distribution becomes uniform. The density distribution is based on the quantity of reflected light at the time outer appearance inspection is carried out. Therefore, a condition on which an outer appearance inspection is visually carried out by an operator can be made proper.

In the present invention, more preferably, a reference density value included in the uniform density distribution is a previously-set density value.

According to the present invention, a reference value is required in the uniform density distribution. More preferably, it suffices that, due to a reference density value being previously set, the quantities of light from all light emitting portions may be increased or decreased so as to become the previously-set density value.

In the present invention, still more preferably, a reference density value included in the uniform density distribution is an average density value of the region whose outer appearance is to be inspected.

According to the present invention, the reference density value included in the uniform density distribution is set as an average density value of a detected density distribution. Therefore, it is not necessary to previously set a reference density.

In the aforementioned aspect of the present invention, further preferably, the surface of the region whose outer appearance is to be inspected is an inner peripheral surface of a concave member.

When the surface of the region whose outer appearance is to be inspected is an inner peripheral surface of a concave member, even if the quantity of emitted light is fixed, a uniform quantity of reflected light is difficult to be obtained. In this case, the effect of the present invention can sufficiently be exhibited.

In the aforementioned aspect of the present invention, still further preferably, the surface of the region whose outer appearance is to be inspected is an inner peripheral surface of a tire.

Particularly in a tire structure, an opening is provided at an inner side of a donut-shaped configuration. Therefore, the quantities of light from the light source units are not difficult to reach to the inner peripheral surface, and are apt to become ununiform. Due to the present invention being applied to the outer appearance inspection for the inner peripheral surface of the tire, there is no possibility that an operator may fail to notice a flaw or the like, or fail to recognize a shadow as a flaw. As a result, inspection efficiency can be improved.

DESCRIPTION OF THE PREFERRED EMBODIMENTS

Figure 1:
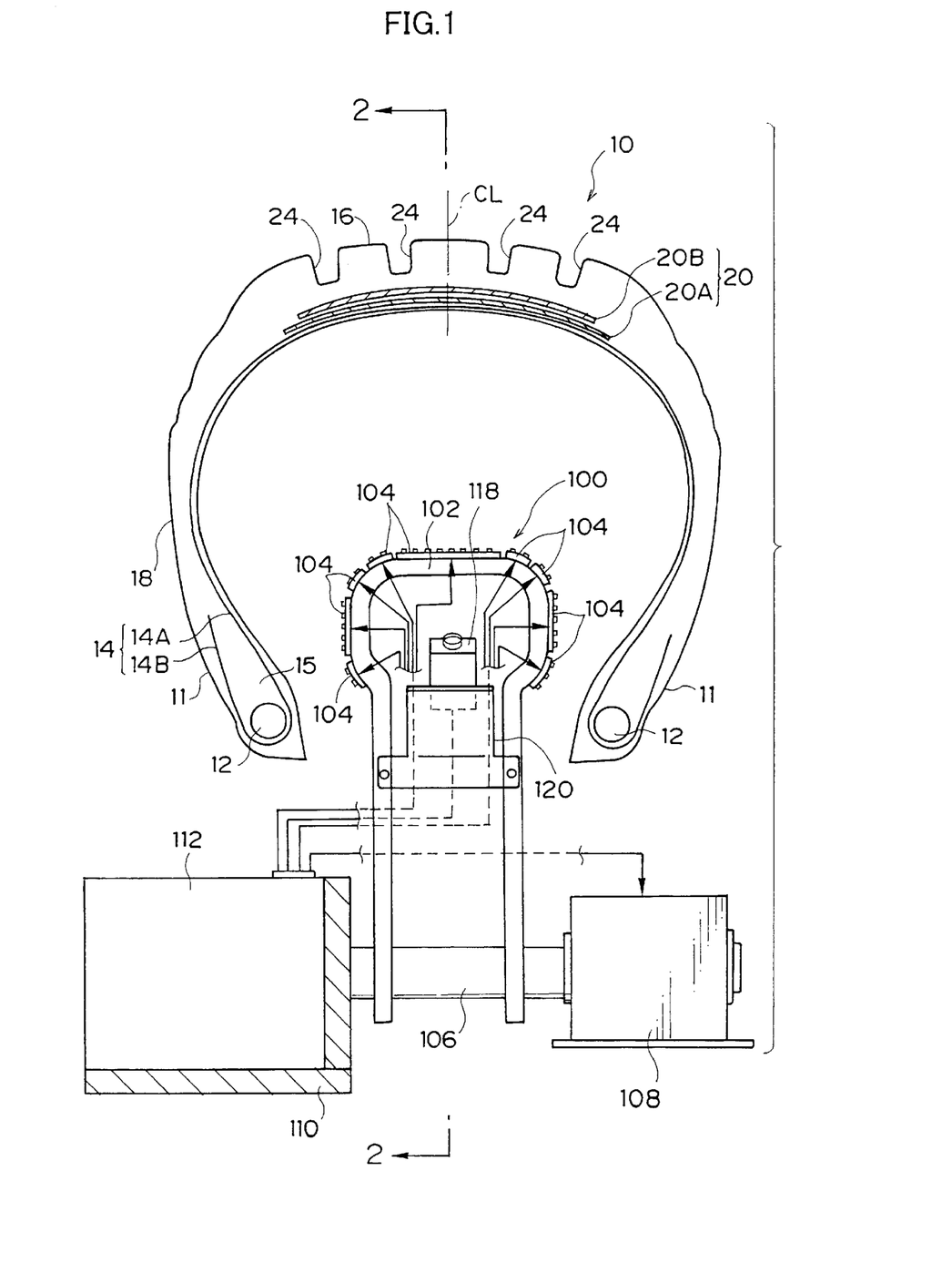
FIG. 1 is a diagram showing a case in which an illuminating apparatus according to an embodiment of the present invention is applied to an illumination used for inspecting the outer appearance of an inner peripheral surface of a tire.

FIG. 1 shows a cross section of a pneumatic radial tire 10 (hereinafter referred to simply as a "tire 10") which is used as a member to be visually inspected by an illuminating apparatus 100 according to an embodiment of the present invention.

The tire 10 includes a carcass 14 engaged with and fastened around a bead core 12 embedded in a bead portion 11 by being folded back from the inside to the outside of the tire, a bead filler 15 disposed between a main body portion 14A and a folded portion 14B of the carcass 14, a tread portion 16 located at a crown portion of the carcass 14, a side wall portion 18 located at a side portion of the carcass 14, and belt layers 20A and 20B having a two-layer structure disposed at the inner side of the tread portion 16.

In the tread portion 16, a plurality of circumferential-direction main grooves 24 are formed so as to extend along a circumferential direction of the tire. In the present embodiment, four main grooves in all, that is, two main grooves are formed at each of both sides of an equatorial plane CL of the tire in FIG. 1.

The production of the tire 10 having the aforementioned structure includes a process of visually inspecting the outer appearance of an inner peripheral surface. In the visual inspection process, in a state in which the tire 10 is mounted in a holding device (not shown), the inner peripheral surface of the tire 10 is illuminated by an illuminating apparatus 100.

The illuminating apparatus 100 is formed by a plurality of light source units 104 held by a substantially U-shaped guide rail 102, and a motor 108 with a rotating shaft 106 mounted at a lower end of the guide rail 102. The end of the rotating shaft 106 of the motor 108 is supported by a bracket 110. A control section 112 for controlling the light source units 104 and the motor 108 is mounted in the bracket 110.

Figure 2:
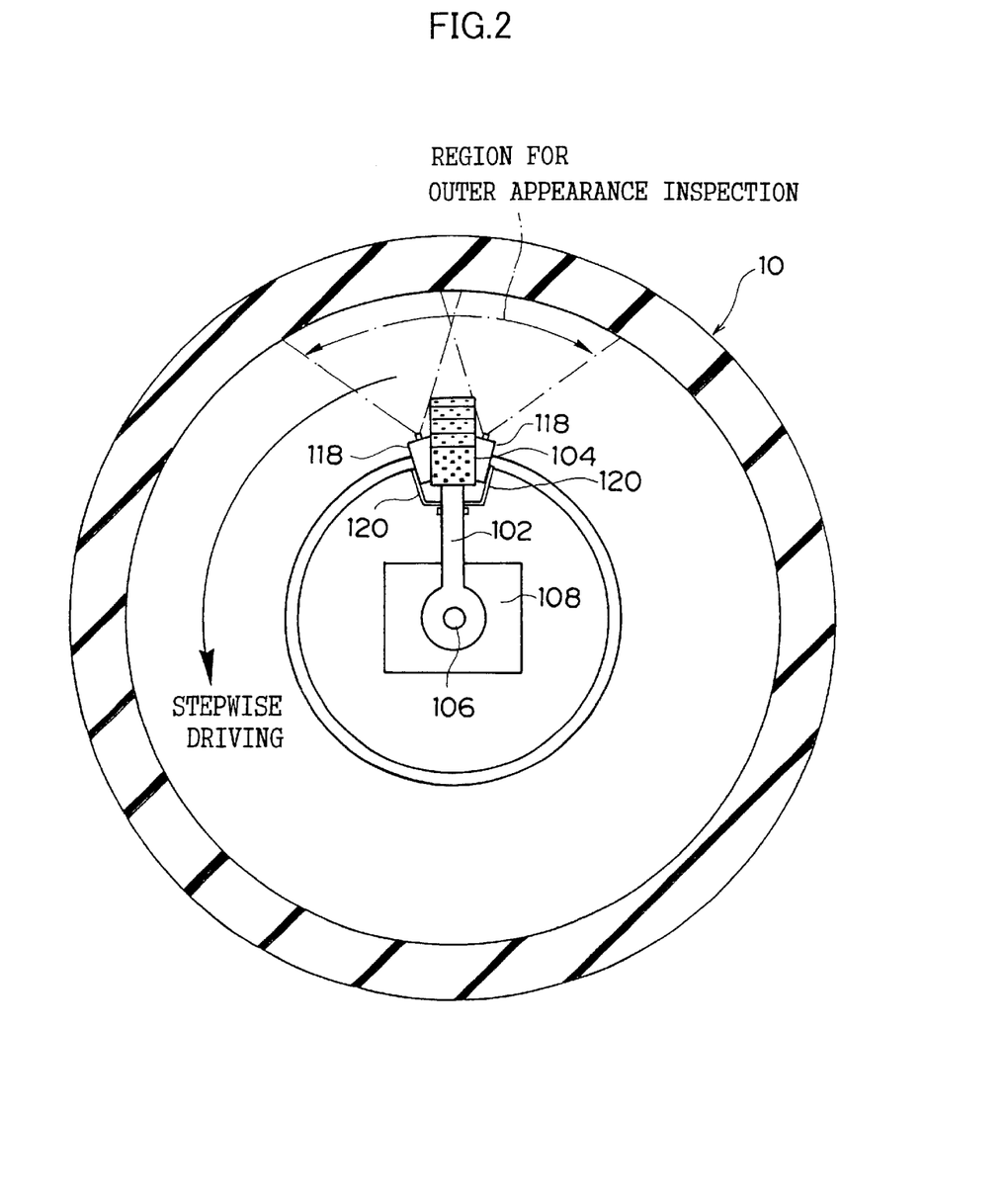
FIG. 2 is a cross-sectional view taken along the line 2—2 in FIG. 1.

As shown in FIG. 2, the motor 108 is driven stepwise by a predetermined angle at a time to cause the light source units 104 to rotate along the inner peripheral surface of the tire 10 in a range of 360 degrees. In other words, a region to be visually inspected is divided into several sections and the divided sections are each illuminated.

In the present embodiment, the light source units 104 are rotated in relation to the tire 10. However, the tire 10 may be rotated by using a rotating mechanism provided in the holding device.

Figure 3:
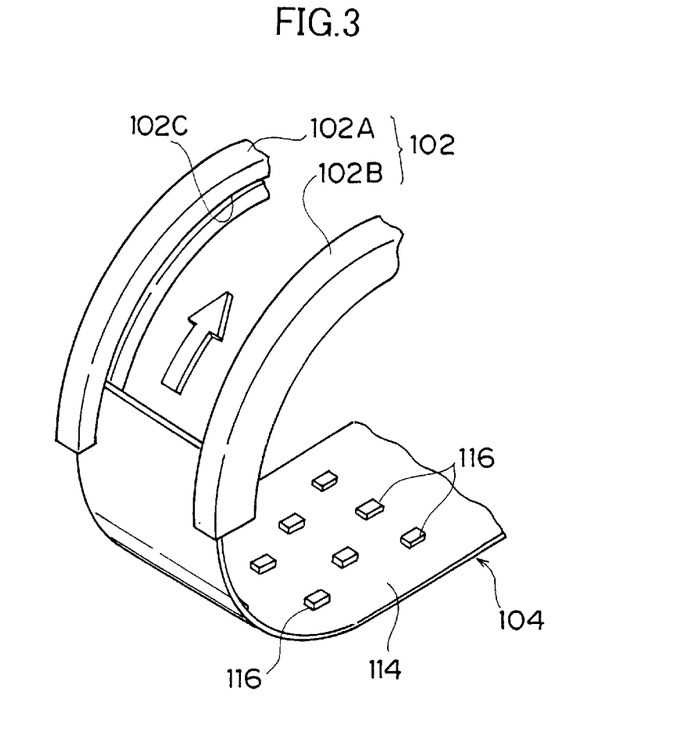
FIG. 3 is a perspective view showing a state in which a guide rail and a light source unit are assembled.

As shown in FIG. 3, the guide rail 102 is formed by a pair of rail portions 102A and 102B facing each other and disposed parallel to each other. Further, the light source unit 104 is formed with a plurality of LEDs 116 mounted on a flexible base plate 114. The light source unit 104 is held in such a manner that both ends of the base plate 114 in the widthwise direction thereof are accommodated in groove portions 102C which are respectively formed on facing surfaces of the pair of rail portions 102A and 102B. In FIG. 3, only a groove portion 102C of the rail portion 102A is shown.

The guide rail 102 is bent so as to have a substantially U-shaped configuration. The plurality of base plates 114 while being bent can be sequentially inserted from lengthwise-direction ends of the rail portions 102A and 102B.

The light source unit 104 thus held can be made to face the inner peripheral surface of the tire 10 at a predetermined space therebetween.

Figure 4:
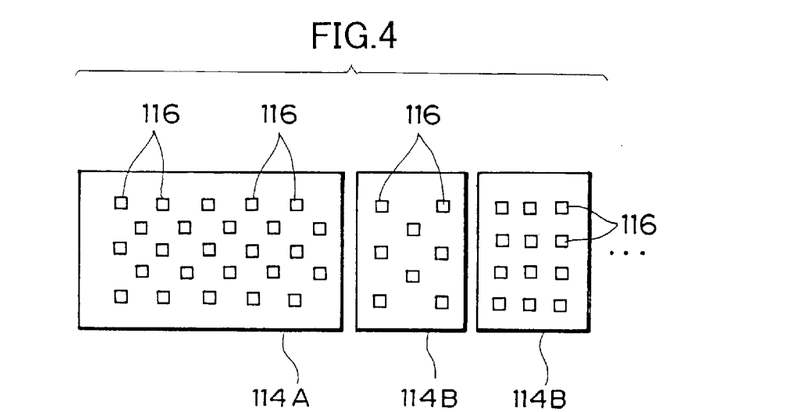
FIG. 4 is a front view showing the type or size of a light source unit.

As shown in FIG. 4, the base plates 114 of the light source units 104 are different in size. A relatively large-sized base plate 114A is used for a low-curvature portion on the inner peripheral surface of the tire 10, and a relatively small-sized base plate 114B is used for a high-curvature portion. In the present embodiment, the number of LEDs 116 mounted on the base plate 114 can be set in the range of 3 to 60.

Due to the base plates 114 being thus arranged, when the LEDs 116 are all turned on in the same quantity of light, a region to be visually inspected on the inner peripheral surface of the tire 10 can be illuminated. The LEDs 116 which emit light of green or blue are most suitable for inspection of the inner peripheral surface of the tire 10, but LEDs which emits light of white or others may also be used.

As shown in FIGS. 1 and 2, a pair of CCD 118 serving as a density detecting device is mounted in the guide rail 102 via brackets 120. The CCD 118 serves as an image pickup for a region to be visually inspected, which region is illuminated by the light source units 104.

Figure 5:
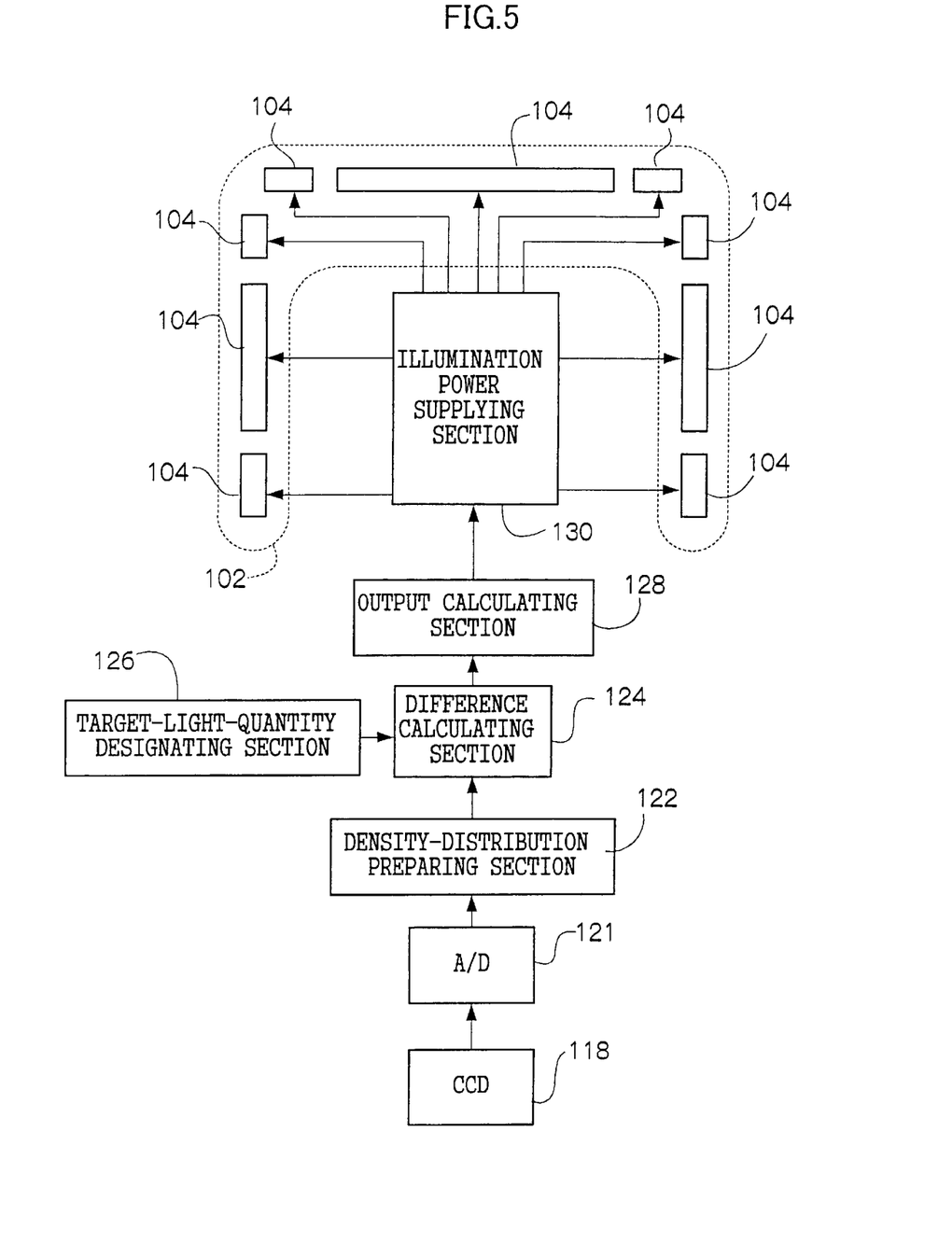
FIG. 5 is a control block diagram for adjustment of light quantity in the illuminating apparatus.

As shown in FIG. 5, the CCD 118 is connected via an A/D converter 121 to a density distribution preparing section 122. In the density distribution preparing section 122, density distribution analysis of the region to be visually inspected is carried out based on data (density data) obtained by pickup with the CCD.

The prepared density distribution data is transmitted to a difference calculating section 124. Target light quantity data from a target-light-quantity designating section 126 is also inputted to the difference calculating section 124. Accordingly, in the difference calculating section 124, a difference between the target light quantity data and each of density distribution data separated for each predetermined field angle is calculated. Separated field angles are classified for each light source unit 104.

The result of calculation in the difference calculating section 124 is transmitted to an output calculating section 128. In the output calculating section 128, the quantity of light emitted from each light source unit 104 is calculated and converted into a current value. The converted value is further delivered to an illumination power supplying section 130.

The illumination power supplying section 130 is allowed to supply a different current for each light source unit 104. Accordingly, the LEDs 116 of each light source unit 104 are turned on based on a current value supplied from the illumination power supplying section 130.

As a result, the light source units 104 have different quantities of emitted light, but the resultant quantity of reflected light from the region to be visually inspected on the tire 10 can be made substantially uniform.

Next, the operation of the present embodiment will be described.

First, an inspection procedure will be explained. The rotating shaft 106 of the motor 108 is set at an initial position and the light source units 104 are supplied with electricity to turn on the LEDs 116. Due to the LEDs 116 being turned on, the region to be visually inspected, which is located at the inner side of the tire 10, can be illuminated. The outer appearance of the illuminated region is visually inspected by an operator for the purpose of checking whether there is a flaw.

When the aforementioned inspection of the region to be visually inspected is completed, the motor 108 is driven to rotate the rotating shaft 106 by a predetermined angle. As a result, the guide rail 102 rotates around the rotating shaft 106 by a predetermined angle and the light source units 104 are located at a position corresponding to an adjacent region to be subsequently visually inspected.

A region illuminated by the LEDs 116 at this time is different from the region for which visual inspection was completed. An operator carries out again an inspection for the subsequent region.

When the aforementioned operation is performed stepwise until a 360-degree rotation of the rotating shaft 106 is completed, an outer appearance inspection for the inner peripheral surface of the tire 10 is completed.

The LEDs 116 are mounted on the flexible base plate 114, which is bent along the bent guide rail 102, and disposed so as to face the inner peripheral surface of the tire 10 at a predetermined space therebetween. Therefore, the light source comprised of the LEDs 116 can be made to face the inner peripheral surface of the tire 10 and illumination light can be spread over the surface.

However, the inner peripheral surface of the tire 10 is made irregular and a portion by which straightly-advancing light is intercepted exists on the surface. For this reason, a shady portion is caused due to illumination light being intercepted by the irregularities, and the quantity of reflected light from the region to be visually inspected on the tire 10 is made ununiform.

In the present embodiment in order to eliminate nonuniformity in the quantity of reflected light, the quantity of light emitted from the LEDs 116 is adjusted, in the control section 112, for each region to be visually inspected based on pickup image data from the CCD 118 for the inner peripheral surface of the tire 10. A description will be hereinafter given of a control routine for light quantity adjustment with reference to FIG. 6.

Figure 6:
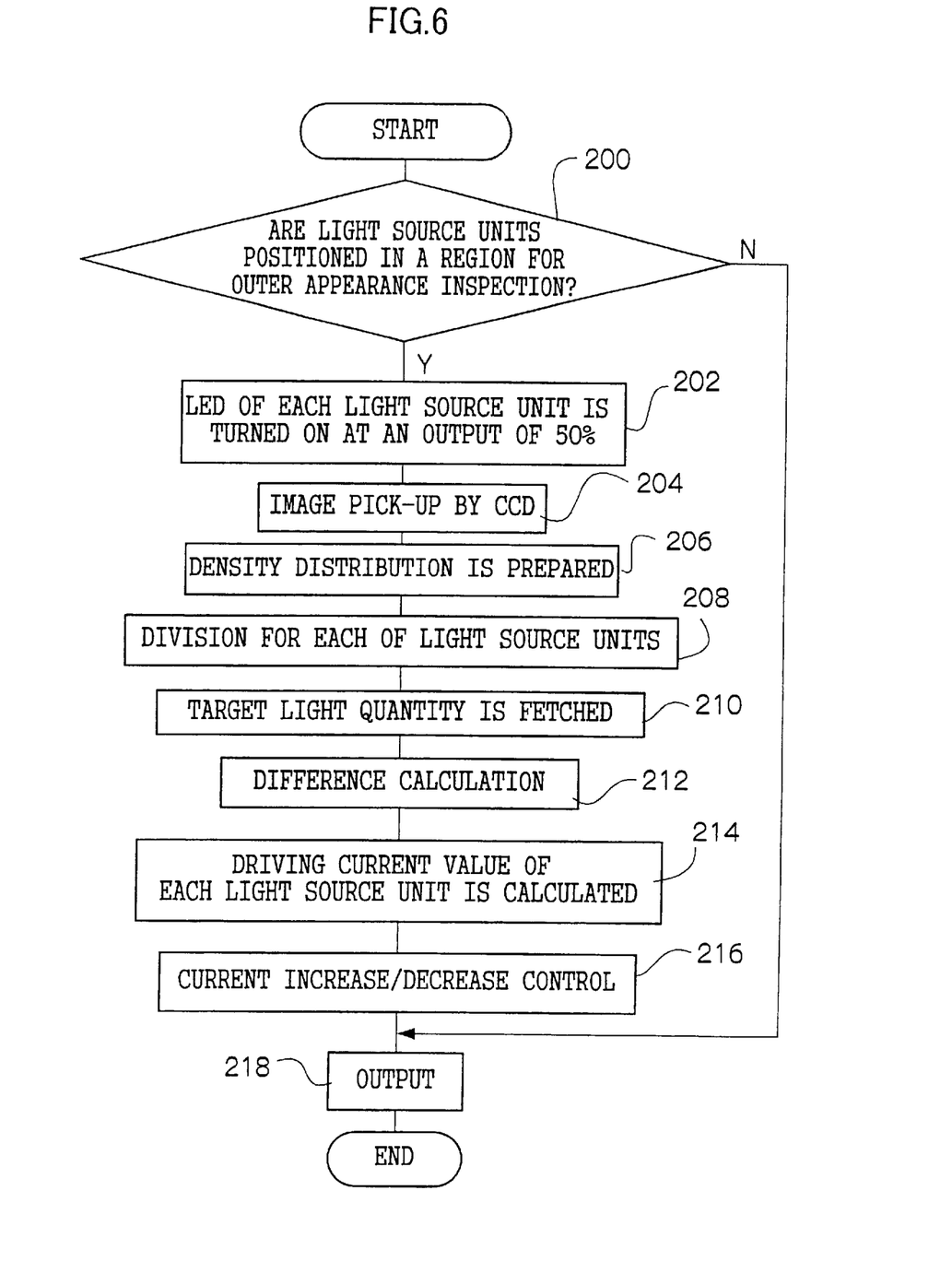
FIG. 6 is a flow chart showing a control routine for adjustment of light quantity in the illuminating apparatus.

First, in step 200, it is determined whether or not the light source units are located in a region to be visually inspected. That is, this determination is made affirmative when the motor 108 is driven to rotate the rotating shaft 106 and the guide rail 102 is located at a predetermined position.

In the subsequent step 202, the LEDs 116 mounted in each light source unit 104 are not turned on in the maximum output, and preferably turned on at a predetermined ratio (for example, 50%). In this case, if the LEDs 116 are turned on at the ratio less than 40% of the maximum output, a sufficient quantity of light is not given. If the LEDs 116 are turned on at the ratio greater than 80%, the range in which an increase in the quantity of light can be controlled is not sufficiently obtained. That is, some latitude is allowed in an output range when the quantity of light is increased in an operation for increase and decrease in the light quantity, which will be described later. So long as such latitude is allowed, the quantity of light from a light emitting portion corresponding to a portion having a high density, in which light quantity is low, can be increased.

When in step 202 the LEDs 116 are turned on, the process proceeds to step 204 and an image is picked up by the CCD 118 from the region to be visually inspected, which region is illuminated by the LEDs 116.

In the subsequent step 206, a density distribution of the quantity of light reflected from the region to be visually inspected is prepared based on the pickup data. Although, at this time, it suffices that the density of the region to be visually inspected is fixed, density unevenness may occur as described above. In other words, a high density region is a portion to which light does not reach, and a low density region is a portion to which light excessively reaches or light converges due to irregular reflection or the like.

In step 208, the prepared density distribution data is divided for each of the plurality of field angles and divided portions are classified for each field angle at which the region to be visually inspected is illuminated by each light source unit 104.

In step 210, target light quantity data previously set is fetched. In the subsequent step 212, a difference between the target light quantity data and light quantity data for each field angle calculated in the aforementioned step 208 is calculated.

In step 214, a driving current value for each light source unit 104 is calculated from the calculated difference. Subsequently, in step 216, the calculated driving current value is transmitted to the illumination power supplying section 130.

In step 218, each light source unit 104 is controlled so as to be turned on based on the calculated driving current value in the illumination power supplying section 130.

As described above, in the present embodiment, an image is picked up by the CCD 118 from the region to be visually inspected, which is illuminated by turning on the LEDs 116, and based on the pickup result, the density distribution of the region to be visually inspected is prepared, and a difference between a target light quantity and a light quantity for each field angle of the density distribution at which the region is illuminated by each light source unit 104, thereby allowing correction of light quantity. As a result, the resultant quantity of light reflected from the region to be visually inspected on the inner peripheral surface of the tire 10 can be made uniform. Accordingly, it is possible for an operator to carry out an outer appearance inspection on a condition of a uniform quantity of light. Further, even if the inner peripheral surface of the tire 10 is made irregular, outer appearance inspection can be properly carried out.

The present embodiment was described in the case of an outer appearance inspection which is visually carried out by an operator, but automatic inspection can be carried out substantially with the same precision as the visual inspection by carrying out the aforementioned adjustment of light quantity.

Figure 7:
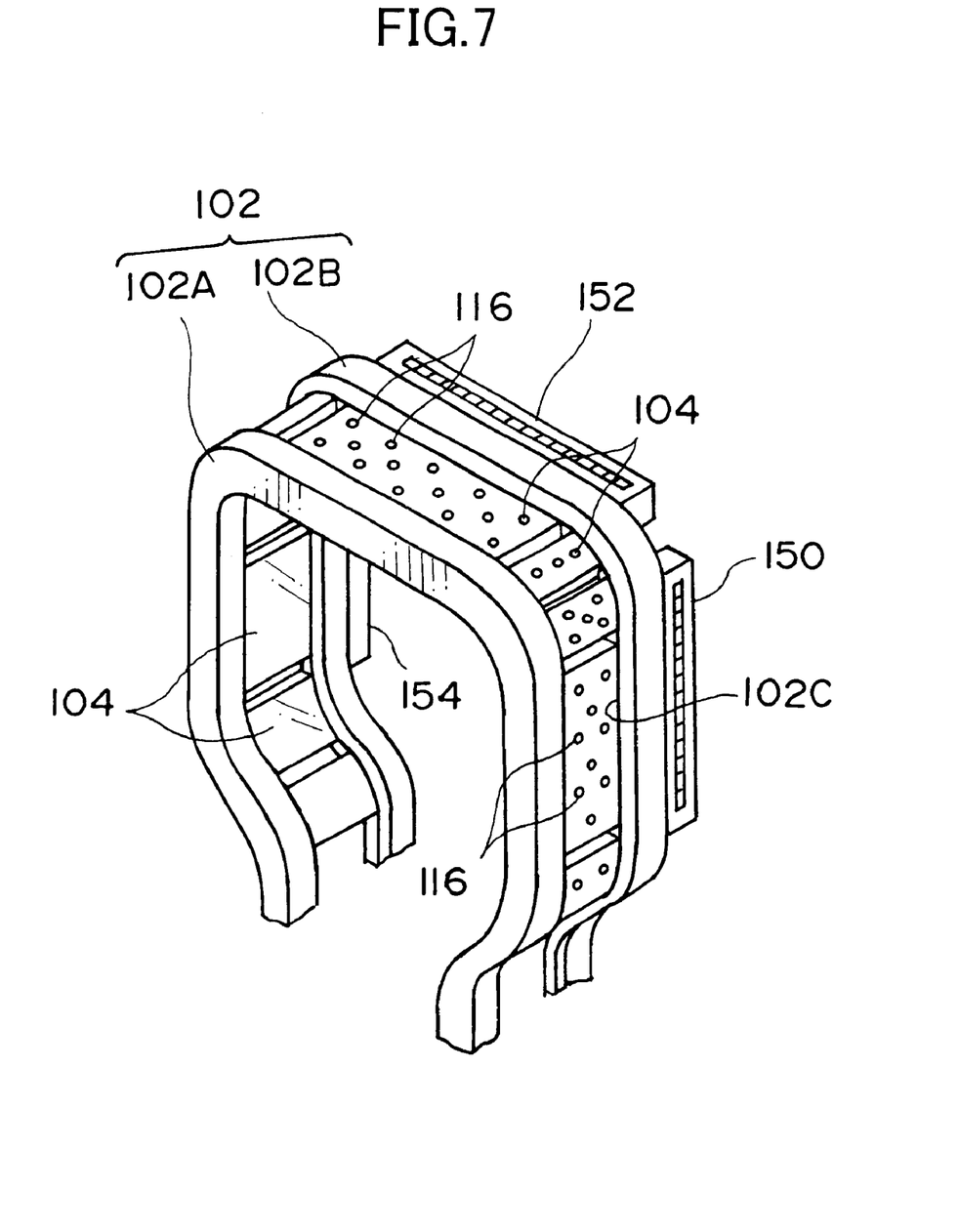
FIG. 7 is a perspective view showing the structure of an illuminating apparatus for automatic inspection according to a modified example.

In other words, conventionally, a surface to be inspected is scanned by a CCD area camera or a CCD linear sensor to allow an image to be picked up therefrom, and a picked-up image density or the like is compared with a reference level, thereby making it possible to determine whether it is good or bad. However, this method lacks reliability because of non-uniformity in the quantity of reflected light. On the other hand, it is possible to maintain reliability by carrying out the adjustment of light quantity explained in the present embodiment. For example, as shown in FIG. 7, CCD linear sensors 150, 152 and 154 are disposed on the side surface of the rail portion 102B so as to face both side surface and bottom surface of a surface to be inspected. When the guide rail 102 is caused to make one revolution in the circumferential direction of the tire, the entire region on the inner peripheral surface of the tire can be scanned by the CCD linear sensors 150, 152 and 154.

Figure 8:
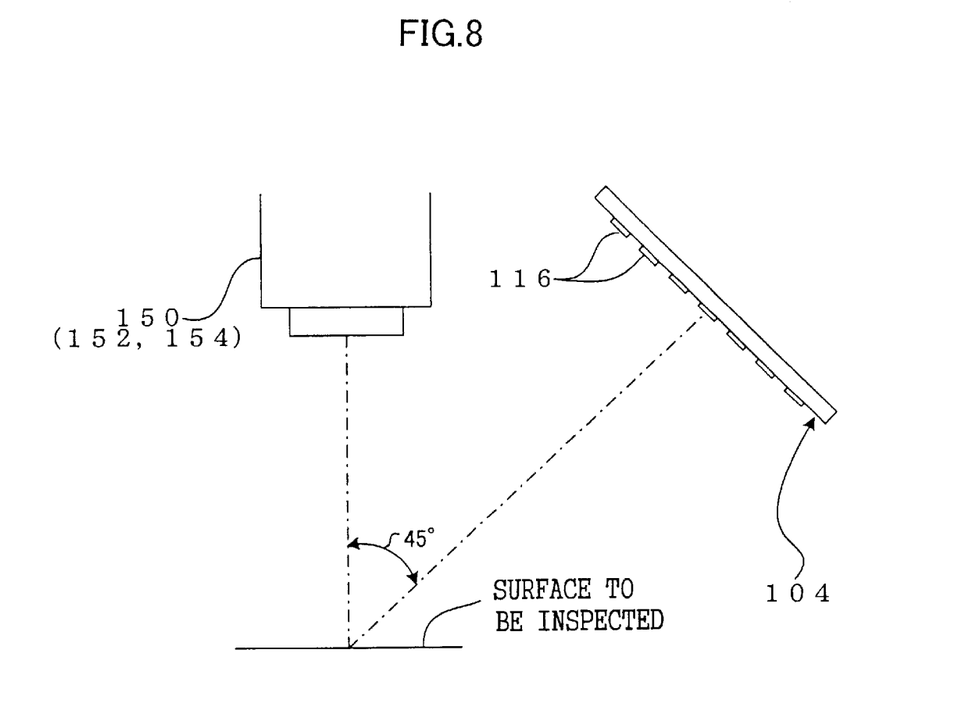
FIG. 8 is a side view showing the relative position relationship between a camera and an illumination.

In this case, as shown in FIG. 8, when an optical axis of a camera for picking up an inspection image is made vertical to the surface to be inspected, and an optical axis of an illumination is made at an angle of 45 degrees with respect to the surface to be inspected, a precision in extracting a flaw on the surface to be inspected can be further raised. As the camera, either an area camera or a linear sensor may be used.

Further, due to a plurality of CCDs 118 being provided so as to correspond to two side surfaces and a bottom surface of the tire inner periphery, read-out resolution can be increased.

In the present embodiment, the density distribution prepared from a result of pickup by the CCD 118 is compared with a target light quantity (difference calculation). However, a difference between an average density calculated from the density distribution and a light quantity for each field angle may be calculated without using the target light quantity. When the quantity of light is not sufficient, the light quantity of each of all light source units may be increased.

Further, the pair of CCDs 118 is used as the density detecting device, but a single CCD may be used. Alternatively, other density sensor may also be used.

Moreover, a device for calculating an output driving current from a density distribution is not limited to difference calculation. For example, an individual turn-on system, fuzzy weight calculation, genetic algorithm or the like can be applied.

In the present embodiment, the illuminating apparatus 100 is applied to an outer appearance inspection for the inner peripheral surface of the tire 10. However, it is not limited to the tire 10 and can also be applied to an outer appearance inspection for inner peripheral surfaces of various concave members.

As described above, the present invention has an excellent effect in that a surface having a curved portion can be uniformly irradiated with light as a surface of which outer appearance is to be inspected and outer appearance inspection can be properly carried out.

What is claimed is:

1. An illuminating apparatus in which when an outer appearance of a surface having a curved surface is inspected, the surface to be inspected is illuminated, comprising:
    an illumination density detecting device which is capable of detecting an illumination density of at least a region whose outer appearance is to be inspected;
    a light source unit provided with a predetermined number of light emitting portions which emit light for illuminating the region whose outer appearance is to be inspected, and also provided with a base plate having the predetermined number of light emitting portions and made of a flexible material, a size of the base plate is dependent on a curvature of the region to be illuminated;
    a locating device for locating the light source unit along a curvature of the surface at a predetermined space to a surface of the region whose outer appearance is to be inspected; and
    an emitted-light-quantity control device for controlling a quantity of light from the light emitting portions based on a result of detection by the illumination density detecting device.

2. The apparatus of claim 1, wherein the emitted-light-quantity control device is formed by:
    an illumination density distribution preparing device for, based on a detection result of illumination density from the illumination density detecting device, preparing an illumination density distribution of the region whose outer appearance is to be inspected; and
    an emitted-light-quantity increase/decrease device for increasing or decreasing a quantity of light emitted from the tight emitting portions so that the illumination density distribution prepared by the illumination density distribution preparing device is made uniform.

3. The apparatus of claim 1, wherein the surface of the region whose outer appearance is to be inspected is an inner peripheral surface of a concave member.

4. The apparatus of claim 1, wherein the surface of the region whose outer appearance is to be inspected is an inner peripheral surface of a tire.

5. The apparatus of claim 2, wherein a reference illumination density value included in the uniform illumination density distribution is a previously set illumination density value.

6. The apparatus of claim 2, wherein a reference illumination density value included in the uniform illumination density distribution is an average illumination density value of the region whose outer appearance is to be inspected.

7. The apparatus of claim 2, wherein the surface having a curved portion has two side surfaces and a bottom surface, and a plurality of light emitting portions are provided so as to correspond to the two side surfaces and the bottom portion.

8. The apparatus of claim 6, wherein the illumination density detecting device has at least one CCD.

9. The apparatus of claim 6, wherein the light emitting portions are LEDs which emit light of green or blue.

10. An illuminating apparatus in which when an outer appearance of a surface having a curved surface is inspected, the surface to be inspected is illuminated, comprising:
   an illumination density detecting device which is capable of detecting an illumination density of at least a region whose outer appearance is to be inspected;
   a light source unit provided with a predetermined number of light emitting portions which emit light for illuminating the region to be inspected, and a base plate having the predetermined number of light emitting portions provided thereon, a size of the base plate is dependent on a curvature of the region to be illuminated;
   a positioning device for positioning the light source unit at a position corresponding to the region whose outer appearance is to be inspected; and
   an emitted-light-quantity control device for controlling a quantity of light from the light emitting portions based on a result of detection by the illumination density detecting device.

11. The apparatus of claim 10, wherein the positioning device includes a motor which is driven in a stepwise manner, and a control section for controlling the light source unit and the motor.

12. The apparatus of claim 10, wherein the surface of the region whose outer appearance is to be inspected is an inner peripheral surface of a concave member.

13. The apparatus of claim 10, wherein the emitted-light-quantity control device is formed by:
   an illumination density distribution preparing device for, based on a detection result of illumination density from the illumination density detecting device, preparing an illumination density distribution of the region whose outer appearance is to be inspected; and
   an emitted-light-quantity increase/decrease device for increasing or decreasing a quantity of light emitted from the light emitting portions so that the density distribution prepared by the illumination density distribution preparing device is made uniform.

14. The apparatus of claim 12, wherein the surface of the region whose outer appearance is to be inspected is an inner peripheral surface of a tire.

15. The illuminating apparatus of claim 13, wherein a reference illumination density value included in the uniform illumination density distribution is a previously set illumination density value.

16. A method for illuminating a curved surface so as to support an inspection for an outer appearance of the curved surface by using an illuminating apparatus having a plurality of light source units, comprising the steps of:
   (a) positioning the illuminating apparatus in at least a portion of a region to be inspected, and when the plurality of light source units are turned on at a predetermined output, performing image pickup from the region to be inspected;
   (b) preparing an illumination density distribution by gathering light illumination density data of a portion corresponding to each light source unit in the region to be inspected; and
   (c) calculating a current value required for each light source unit by using the illumination density distribution for each light source unit.

17. The method of claim 16, wherein the step of carrying out a calculation comprises the step of preparing an illumination density distribution and comparing it with a target light quantity.

18. The method of claim 16, wherein the step of carrying out a calculation further comprises the step of calculating an average illumination density from the illumination density distribution, and calculating a difference in light quantity between the average illumination density and the illumination density data of a portion corresponding to each light source unit.

19. The method of claim 16, wherein the light source units are turned on in a ratio of 40% to 80% of a maximum output state.

20. The method of claim 19, further comprising the step of correcting positions of the light source units by using a result of the calculation in the step of carrying out a calculation.

* * * * *